United States Patent [19]
Gerhold

[11] B 3,992,469
[45] Nov. 16, 1976

[54] EFFLUENT FRACTIONATION IN SIMULATED MOVING-BED ADSORPTION PROCESSES

[75] Inventor: Clarence G. Gerhold, Palatine, Ill.

[73] Assignee: Universal Oil Products Company, Des Plaines, Ill.

[22] Filed: Aug. 5, 1974

[21] Appl. No.: 494,944

[44] Published under the second Trial Voluntary Protest Program on February 17, 1976 as document No. B 494,944.

[52] U.S. Cl. .......................... 260/674 SA; 203/41; 208/310 R; 208/310 Z
[51] Int. Cl.² .................. C07C 7/12; C07C 7/13
[58] Field of Search ............. 260/674 SA; 208/310; 203/41

[56] References Cited
UNITED STATES PATENTS

| | | | |
|---|---|---|---|
| 2,576,525 | 11/1951 | Lipkin | 260/674 |
| 2,790,016 | 4/1957 | Lanneau | 260/674 |
| 3,510,423 | 5/1970 | Neuzil et al. | 208/310 |
| 3,636,121 | 1/1972 | Stine et al. | 260/674 |

Primary Examiner—Delbert E. Gantz
Assistant Examiner—C. E. Spresser
Attorney, Agent, or Firm—James R. Hoatson, Jr.; Robert W. Erickson; William H. Page, II

[57] ABSTRACT

There is a drastic change in the composition of the effluent streams of a fixed bed adsorption column when the feed and withdrawal points are periodically advanced in order to simulate moving-bed operation. These effluents are fractionated to recover a desorbent which is recycled to the adsorption column. The claimed process improves the efficiency of this fractionation by changing the locations at which the effluents enter the fractionators to correlate the compositions of the effluents and the material in the fractionators at these locations.

8 Claims, 1 Drawing Figure

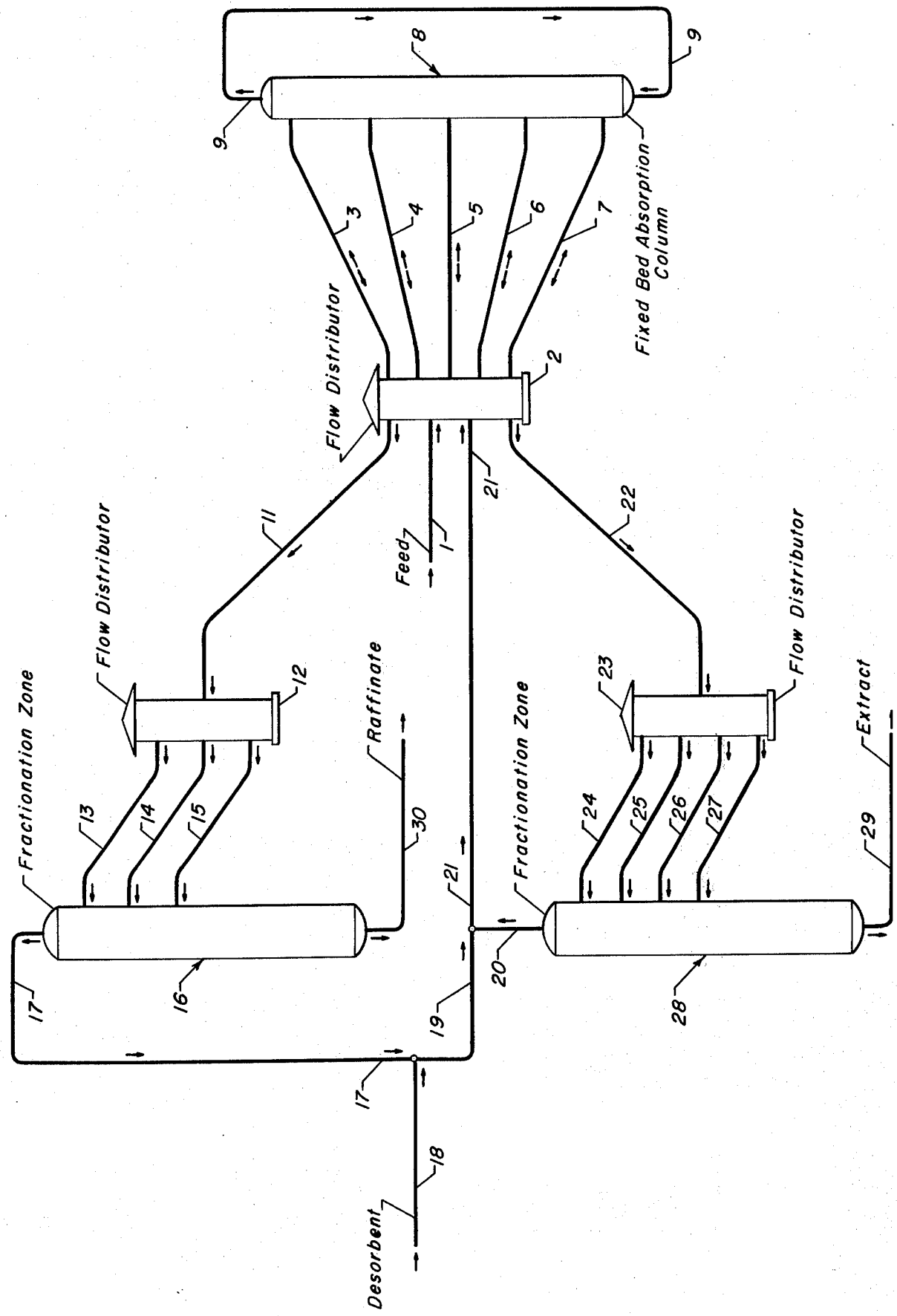

3,992,469

EFFLUENT FRACTIONATION IN SIMULATED MOVING-BED ADSORPTION PROCESSES

BACKGROUND OF THE INVENTION

1. Field of the Invention

The invention relates to an improvement in a process for the separation of hydrocarbons which utilizes the preferential adsorbency of a solid material, such as a molecular sieve, to perform the separation. The separation process may be further characterized as one in which a moving-ged of adsorbent is simulated by periodically advancing the points at which the feed, desorbent and effluent streams are communicated with a fixed bed of adsorbent. The invention specifically relates to the manner in which the effluent streams of the bed of adsorbent are fractionated in order to recover the desorbent and purify the product streams.

2. Description of the Prior Art

Separation processes using a solid adsorbent and in which the transfer points of the feed streams, desorbent streams and effluent streams are periodically advanced in a unidirectional manner to simulate the action of a moving-bed of adsorbent are known to the art. Typical processes are shown in United States Pat. Nos. 3,201,491 (Cl. 260-676) and 3,274,099 (Cl. 208-310). In U.S. Pat. No. 3,510,423, the operation of such a process is further described, including the use of a flow distributor to periodically change the lines carrying the various process streams associated with the adsorption column. This reference teaches fractionating both the raffinate-containing effluent stream and the extract-containing effluent stream to recover the desorbent for reuse in the adsorption column.

When the points at which the raffinate-containing and the extract-containing effluent streams are removed from the column are changed, the composition of these streams takes a sudden step-like change toward a higher desorbent content. This sudden increase in what is normally the more volatile of the two components separated in the fractionation zone would cause an upset in the operation of the fractionation zone if uncorrected. To counteract this problem, the prior art has placed an accumulation zone in the effluent flow path between the flow distributor and the fractionation zone. The backmixing in this zone produces a uniform charge stock for the fractionation zone.

It is known in the art of fractionation that to obtain the best possible separation in an existing fractionation column, it is necessary to introduce the feed stream at a point determined by the condition of the feed stream and the composition of the liquid on different trays in the column. See for instance page 13–39 of *The Chemical Engineer's Handbook*, John H. Perry Ed., 4 Ed., McGraw-Hill, 1963.

BRIEF SUMMARY OF THE INVENTION

The invention comprises replacing the prior art effluent backmixing zone by a flow distributor means which changes the position at which the effluent streams enter the fractionation zones. By correlating the composition of the effluent and the composition of the liquid in the fractionation zone, the amount of separation required in the fractionation zone is decreased and the operation of the fractionation zone is not disturbed by sudden changes in the composition of the material charged to it.

DESCRIPTION OF THE DRAWING

The drawing illustrates the preferred embodiment of the invention. A multi-component hydrocarbon feed stream enters a separation process through line 1. Flow distributor 2 channels the feed stream into one of lines 3, 4, 5, 6 or 7 depending upon the position of the cycle at the exact time at which the feed stream enters the flow distributor. The flow of the feed stream in line 1 is continuous and the flow of the feed stream into the fixed bed adsorption column 8 is also continuous. The feed stream will be sequentially channeled through each of lines 3–7 in a preprogrammed cycle which starts with line 7 and ends with line 3. This cycle is repeated continuously, and the flow is switched from line 3 to line 7 whenever a new cycle begins. These same lines also carry the effluent streams from the adsorption bed, and the direction of the flow will depend on the position of the cycle. Line 9 carries a pump-around liquid stream connecting the two ends of the adsorption column and providing means for continuous liquid passage through the adsorption column.

Lines 3–7 divide the adsorption column into a number of zones in which different operations such as adsorption, desorption and flushing are performed. There is a continuous flow of a desorbent liquid into the adsorption column. This desorbent stream enters the adsorption column at a point which is two zones beyond that which the feed point enters the column. For instance, if the feed stream is entering the adsorption column through line 6, then a desorbent stream is entering the column through line 4. This operation produces two effluent streams. There is a raffinate-rich effluent stream leaving the adsorption column through line 5 and an extract-rich effluent stream leaving the adsorption column through line 3. Both of these effluent streams enter flow distributor 2, with the extract-rich stream being channeled into line 22 and the raffinate-rich effluent stream being channeled into line 11. The raffinate-rich effluent stream is then passed into a second flow distributor 12 which further channels the flow of this stream through either lines 13, 14 or 15. These three lines charge the raffinate-rich effluent stream into a first fractionation zone 16 at a point which has been selected, through the proper operation of the second flow distributor 12, to correlate the composition of the entering raffinate-rich stream with the composition of the contents of the fractionation zone 16 at the selected point. A substantially pure stream of the raffinate is removed from the bottom of the fractionation zone through line 30, and a substantially pure stream of desorbent is removed from the top of the fractionation zone through line 17. Make-up desorbent is added to line 17 through line 18 to form the desorbent stream flowing through line 19.

The extract-rich effluent stream flowing through line 22 is passed into a third flow distributor 23. This flow distributor channels the flow of the extract-rich effluent stream into either line 24, 25, 26 or 27. These four lines direct the extract-rich effluent stream into a second fractionation zone 28 in a manner similar to the first fractionation zone. Distillation within the second fractionation zone produces a substantially pure stream of extract material which is removed as a bottoms product through line 29. The distillation also produces a substantially pure stream of desorbent which is removed from the second fractionation zone through line 20. The stream of desorbent from the second fractionation zone is combined with a stream of desorbent in line 19 to form the desorbent stream passing through line 21, and this stream is then charged to the adsorption column 8 through flow distributor 2.

DETAILED DESCRIPTION

The necessity of separating various types of hydrocarbons having similar boiling points and volatilities has led to the development of a number of other separatory processes. One of the most useful of these processes utilizes the ability of certain solid materials to preferentially adsorb a species of molecules having a certain characteristic structure. For example, it is possible with this method to effect the separation of straight chain olefins from straight chain paraffins having the same number of carbon atoms per molecule. It is also possible to separate aromatic hydrocarbons from paraffinic hydrocarbons or to separate specific aromatic isomers, such as separating paraxylene from a mixture of xylene isomers.

The heart of these processes is the selective adsorbent. This may be a naturally occurring substance, but will normally be a synthetically manufactured zeolite because of their greater selectivity and capacity. For instance, the separation of olefins from paraffins can be effected through the use of modified molecular sieve adsorbents as disclosed in U.S. Pat. Nos. 2,071,933 (Cl. 260-677) and 2,265,750 (Cl. 260-666). The manufacture of an especially useful copper-exchange type Y zeolite is described in U.s. Pat. No. 3,720,604 (Cl. 208-310). The adsorbents are generally crystalline aluminosilicates modified with a metal such as silver, potassium, barium or cobalt. Both type X and type Y crystalline aluminosilicates may be used for the separation of aromatic hydrocarbons. A suitable adsorbent for this operation is described in U.S. Pat. No. 3,696,107. The manufacture and use of these adsorbents is well known to those skilled in the art, and they may be purchased commercially.

These selective adsorption processes have become more acceptable for large scale industrial separations with the development of methods of continuous operation. These methods include the continuous movement of a column of the adsorbent through a series of zones wherein the various steps of adsorption, desorption and flushing are performed. However, various problems such as moving the adsorbent, the attrition of the adsorbent and maintaining continuous operation have prevented the widespread acceptance of this approach. The process of the invention is directed to a second method of continuous operation wherein the points at which the various streams entering an elongated bed of the adsorbent are periodically advanced in equal increments. This results in a unilateral migration of the various zones through the bed of adsorbent in a manner which simulates the usage of a moving-bed of the adsorbent. The invention is therefore applicable to processes such as described in U.S. Pat. Nos. 3,201,491 and 3,696,107.

A commercial adsorption unit is somewhat different from the simplified drawing presented to illustrate the principles of the process. For instance, there will be a greater number of the combination feed and withdrawal lines than the five indicated in the drawing. Also, the bed of adsorbent may be of such a large size that a single column becomes impractical. For example, one typical commercial unit has two chambers or columns of adsorbent with twenty-four separate feed points on each chamber. The locations of the zones in which the preferential adsorption and the following desorption and flushing operations are performed gradually move through the bed of adsorbent. They are therefore definable only in terms of the location of the points at which the relevent streams enter the process. A typical zone will comprise a portion of the column which includes several of the combination feed-withdrawal points. For instance, the adsorption zone may consist of that portion of the adsorbent located between six consecutive feed-withdrawal points. This provides for greater continuity of the operation as the total zone is not shifted in any one operation. The intermediate feed-withdrawal points are of course not used.

During the course of the process, a feed stream enters the adsorption zone and travels downstream losing the selected components to the adsorbent. When this stream reaches the withdrawal point which terminates the zone, it is removed as a raffinate-rich stream. When the location of the feed and withdrawal points are shifted, this raffinate-rich stream sweeps a new section of the column located between the old withdrawal point and the new withdrawal point. At the time the withdrawal points are shifted, the new section of the column contains essentially pure desorbent liquid. The first material which leaves at the new withdrawal point therefore has a very high concentration of desorbent. This concentration gradually changes to substantially pure raffinate as the operation progresses. The periodic shifting of the withdrawal points needed to simulate moving-bed operation therefore results in the raffinate-rich stream having a saw-tooth concentration versus time correlation. This same sharp composition change also occurs in the extract-rich stream which is formed in the same manner in a different zone.

Both the raffinate-rich stream and the extract-rich stream are normally fractioned to recover the desorbent and to fractionated the respective product streams. This is described in U.S. Pat. No. 3,510,423. The desorbent is normally chosen to be quite a bit more volatile than either the extract or raffinate to allow its easy separation by fractionation. The previously described rapid changes in the composition of the raffinate-rich stream and the extract-rich stream upset the fractionation columns if these streams are charged directly to the column. The prior art has solved this problem by placing a mixing zone in the path of each of these effluent zones to produce enough backmixing to smooth out the composition of the effluent streams. It is an objective of this invention to provide a process which eliminates the need for such a mixing zone. It is a further objective to increase the efficiency of the fractionation of the effluent streams. The objectives of the invention are obtained and upsets in the operation of the fractionation zones are avoided in the process of the invention by choosing the point at which the effluent stream enters the fractionation zone so to correlate the composition of the material entering the fractionation zone with the composition of the contents of the fractionation zone. It is therefore not required to backmix the effluent streams. Furthermore, the amount of fractionation required is reduced since the relatively pure desorbent enters the fractionation columns close to where the desorbent is removed. This is also true for the extract and raffinate materials. From this it is observed that the invention includes a realization that the mixing zones are accomplishing a purpose which is contrary to the function of the fractionation zones.

The number and the location of the points at which the effluent streams will enter the fractionation zones may be determined by an optimization process known to those skilled in the art of fractionation. It is very likely that they may differ in both of these aspects from the representation in the drawing. If there is any significant time period available between the advancement of the zones in the adsorption column, the composition of the effluents will range widely. The optimum points to inject the effluent streams can therefore be expected to range from near the top of the fractionation column to near the bottom of the column. The operating conditions used within the fractionators is dependent on the materials involved and is also within the expertise of those involved in the design of such units.

The preferred embodiment of the invention may therefore be characterized as a process for the separation of hydrocarbons which comprises the steps of passing a multi-component hydrocarbon feed stream through a first flow distribution means; passing the feed stream from the first flow distribution means and into an adsorption column containing a fixed bed of a solid adsorbent at a first preselected point in the adsorption column; withdrawing an extract-rich effluent stream at a second preselected point in the adsorption column; periodically operating the first flow-distribution means to effect a movement of the location of the first and second preselected points in the adsorption column in a unidirectional pattern which simulates the utilization of a moving-bed of the solid adsorbent by an intermittent shifting of the locations of adsorption and desorption zones within the adsorption column; passing the extract-rich effluent stream through the first flow-distribution means and a second flow-distribution means and into a first fractionation zone; and, effecting a correlation of the composition of the extract-rich effluent stream entering the first fractionation zone with the composition of the contents of the first fractionation zone at the location at which the extract-rich effluent stream enters the first fractionation zone by changing the locations at which the extract-rich effluent stream enters the first fractionation zone through the operation of the second flow-distribution means.

The operation of fractionation columns can also be upset by rapid changes in the temperature or quantity of the liquid entering the column or by a change in feed location. To avoid any of these sources of disturbance, the effluent streams may be first charged into a number of reservoirs which in turn feed particular points in the fractionation columns at a uniform rate. Each reservoir receives only that portion of the effluent stream having a composition range corresponding to the point in the fractionation zone which it feeds. The rate at which each reservoir drains into the fractionation zone is set at a constant rate equal to the amount of liquid fed to the reservoir per movement of the respective adsorption zone divided by the time between these movements.

Three separate flow distribution means are indicated in the drawing. They may, however, be grouped or interconnected either mechanically or electrically into a single integrated apparatus, or into two separate units with the second unit handling both effluent streams. The rate of change of the composition of the two effluent streams will be substantially equal if the volumetric flow rates of these streams are equal. In this fortuitous situation, the optimum injection points into the two fractionation zones will change at the same time. The flow distribution means for the raffinate-rich effluent stream and for the extract-rich effluent stream may therefore be directly connected and actuated by the same driving means. In this mode, a preprogrammed cycle of these secondary flow distribution means will be actuated by the movement of the main flow distribution means which controls the streams flowing through the adsorbent. These flow distribution means may consist of a rotary valve as shown in U.S. Pat. No. 3,201,491 or a more typical multiple-valve manifold system etc. The operation of the secondary flow distribution means may also be controlled by an on-stream analysis of the two effluent streams. This analysis can be made in terms of any distinguishing physical property such as refractive index, resistivity, dialectic constant or thermal conductivity, etc. Either of these two modes of operation may be used to correlate the composition of that portion of the effluent stream fed to a particular location in a fractionation zone with the composition of the liquid material on the fractionation trays at that location.

I claim as my invention:

1. In a process for the separation of hydrocarbons wherein:
   i. a feed stream is passed into a fixed bed of a solid adsorbent which preferentially adsorbs one hydrocarbon species contained in the feed stream;
   ii. an extract-rich effluent stream and a raffinate-rich effluent stream are withdrawn from the bed of solid adsorbent;
   iii. the points at which the feed stream enters the bed of solid adsorbent and at which the effluent streams are withdrawn are periodically moved in a unidirectional pattern which simulates the utilization of a moving-bed of the adsorbent by shifting the location of the adsorption and desorption zones within the adsorption column; and,
   iv. the effluent streams are passed into fractionation zones; the improvement which comprises passing each of the effluent streams through a flow distribution means which changes the locations at which the effluent stream enters the fractionation zone and effects a correlation of the composition of the effluent stream with the composition of the liquid contents of the fractionation zone at the respective location.

2. A process for the separation of hydrocarbons which comprises the steps of:
   a. passing a multi-component hydrocarbon feed stream through a first flow distribution means;
   b. passing the feed stream from the first flow distribution means and into an adsorption column containing a fixed bed of a solid adsorbent at a first preselected point in the adsorption column;
   c. withdrawing an extract-rich effluent stream at a second preselected point in the adsorption column;
   d. periodically operating the first flow distribution means to effect a movement of the location of the first and second preselected points in the adsorption column in a unidirectional pattern which simulates the utilization of a moving-bed of the solid adsorbent by an intermittent shifting of the locations of adsorption and desorption zones within the adsorption column;
   e. passing the extract-rich effluent stream through the first flow-distribution means and a second flow-distribution means and into a first fractionation zone; and, f. effecting a correlation of the composition of the extract-rich effluent stream entering the first fractionation zone with the composition of the contents of the first fractionation zone at the location at which the extract-rich effluent stream enters the first fractionation zone by changing the locations at which the extract-rich effluent stream enters the first fractionation zone through the operation of the second flow distribution means.

3. The process of claim 2 further characterized in that a raffinate-rich effluent stream is withdrawn from the adsorption column, passed through a flow distribution means and into a second fractionation zone.

4. The process of claim 3 further characterized in that the raffinate-rich effluent stream is passed through the second flow distribution means.

5. The process of claim 2 further characterized in that the feed stream comprises xylene isomers.

6. The process of claim 2 further characterized in that the feed stream comprises a mixture of normal paraffins and normal olefins having the same number of carbon atoms per molecule.

7. The process of claim 2 further characterized in that the correlation of the composition of the extract-rich effluent stream entering the first fractionation zone with the composition of the contents of the first fractionation zone at the location at which the extract-rich effluent stream enters the first fractionation zone is controlled by mechanically interconnecting the first flow distribution means with the second flow distribution means and beginning a programmed cycle of operation of the second flow distribution means whenever the first flow distribution is operated to shift the second preselected point at which the extract-rich effluent stream is withdrawn from the adsorption column.

8. The process of claim 2 further characterized in that the correlation of the composition of the extract-rich effluent stream entering the first fractionation zone with the contents of the first fractionation zone at the location at which the extract-rich effluent stream enters the first fractionation zone is controlled by means of an onstream analysis of the extract-rich effluent stream.

* * * * *